(12) United States Patent
Olichney et al.

(10) Patent No.: US 12,023,203 B2
(45) Date of Patent: Jul. 2, 2024

(54) FORCE LIMITING ASSEMBLY FOR SURGICAL INSTRUMENT

(71) Applicant: Conmed Corporation, Utica, NY (US)

(72) Inventors: Michael Olichney, Castle Rock, CO (US); Mason Williams, Centennial, CO (US); Julia Concelman, Greenwood Village, CO (US)

(73) Assignee: Conmed Corporation, Utica, NY (US)

( * ) Notice: Subject to any disclaimer, the term of this patent is extended or adjusted under 35 U.S.C. 154(b) by 973 days.

(21) Appl. No.: 16/967,557

(22) PCT Filed: Feb. 6, 2019

(86) PCT No.: PCT/US2019/016760
§ 371 (c)(1),
(2) Date: Aug. 5, 2020

(87) PCT Pub. No.: WO2019/157000
PCT Pub. Date: Aug. 15, 2019

(65) Prior Publication Data
US 2021/0085418 A1    Mar. 25, 2021

Related U.S. Application Data

(60) Provisional application No. 62/626,854, filed on Feb. 6, 2018.

(51) Int. Cl.
*A61B 90/00* (2016.01)
*A61B 17/29* (2006.01)

(52) U.S. Cl.
CPC .......... *A61B 90/03* (2016.02); *A61B 17/2909* (2013.01); *A61B 2017/2901* (2013.01); *A61B 2017/2919* (2013.01); *A61B 2090/033* (2016.02)

(58) Field of Classification Search
CPC ................ A61B 90/03; A61B 17/2909; A61B 2017/2901; A61B 2017/2919;
(Continued)

(56) References Cited

U.S. PATENT DOCUMENTS

| | | | | |
|---|---|---|---|---|
| 4,218,821 A | * | 8/1980 | Schneider | ................. B25B 7/08 30/254 |
| 5,562,655 A | * | 10/1996 | Mittelstadt | ......... A61B 17/2909 606/1 |

(Continued)

FOREIGN PATENT DOCUMENTS

| | | |
|---|---|---|
| DE | 4411099 | 10/1995 |
| DE | 29713490 | 10/1997 |

(Continued)

OTHER PUBLICATIONS

International Search Report Form PCT/ISA/220, International Application No. PCT/US19/16760, pp. 1-10, dated May 27, 2019.

*Primary Examiner* — Lynsey C Eiseman
*Assistant Examiner* — Christopher J Mutchler
(74) *Attorney, Agent, or Firm* — Bond, Schoeneck & King, PLLC; Frederick J. M. Price

(57) ABSTRACT

A force limiting assembly for a surgical instrument that has a handle and a lever pivotally mounted to the handle at a pivot point for movement of an internal drive shaft. The lever is coupled to the drive shaft by a cantilever spring that is positioned within the lever. The free end of the cantilever is spaced apart from the pivot point of the lever and coupled to the drive shaft via stops positioned on the drive shaft on either side of the free end of the cantilever spring. As the lever is pivoting by a user, the forces move the drive shaft and bias the cantilever spring, thereby reducing and ultimately limiting the amount of force that a user may apply to the drive shaft via operation of the lever.

13 Claims, 10 Drawing Sheets

(58) Field of Classification Search
CPC ...... A61B 2090/033; A61B 17/320092; A61B 2017/2912; A61B 2017/2917; A61B 2018/1455; A61B 2090/031; A61B 2090/065; A61B 18/1445; A61B 17/29; A61B 17/1285; A61B 2017/2932; A61B 2018/0063

See application file for complete search history.

(56) References Cited

U.S. PATENT DOCUMENTS

| | | | |
|---|---|---|---|
| 9,492,225 B2* | 11/2016 | Dycus | A61B 18/085 |
| 9,592,089 B2* | 3/2017 | Lyons | A61B 90/03 |
| 9,808,246 B2* | 11/2017 | Shelton, IV | A61B 17/072 |
| 9,943,325 B2 | 4/2018 | Faller et al. | |
| 2002/0002380 A1* | 1/2002 | Bishop | A61B 17/320092 606/169 |
| 2007/0073314 A1* | 3/2007 | Gadberry | A61B 17/1285 606/142 |
| 2011/0301606 A1* | 12/2011 | Kerr | A61B 18/1445 606/52 |
| 2012/0184989 A1* | 7/2012 | Twomey | A61B 18/1445 606/206 |
| 2013/0053831 A1* | 2/2013 | Johnson | A61B 17/2909 606/1 |
| 2017/0181789 A1* | 6/2017 | Ding | A61B 18/1445 |
| 2017/0245921 A1* | 8/2017 | Joseph | A61B 18/1445 |
| 2018/0042637 A1* | 2/2018 | Craig | G10K 11/22 |
| 2020/0383557 A1* | 12/2020 | Sedlacek | A61B 1/005 |

FOREIGN PATENT DOCUMENTS

| | | |
|---|---|---|
| EP | 0908152 | 4/1999 |
| EP | 3095399 | 1/2017 |
| EP | 3257454 | 12/2017 |
| EP | 3281588 | 2/2018 |

* cited by examiner

FORCE LIMITING ASSEMBLY FOR SURGICAL INSTRUMENT

CROSS-REFERENCES TO RELATED APPLICATIONS

This application is a national stage application under 35 U.S.C. 371 based on international patent application PCT/US19/16760 filed on Feb. 6, 2019, which claims priority to U.S. Provisional Patent Application Ser. No. 62/626,854, filed on Feb. 6, 2018.

BACKGROUND OF THE INVENTION

1. Field of the Invention

The present invention to surgical instrument and, more specifically, to a handle assembly for a surgical instrument that limits the amount of force a user can supply to the jaws of the surgical device.

2. Description of the Related Art

A surgical instrument, such as an electrosurgical vessel sealer, may have a pair of jaws that are closed over tissue in response to a user operating a lever coupled to the handle of the surgical instrument. In order to control the amount of force delivered to the jaws and thus reduce the risk of a user damaging the instrument during use or damaging the target tissue, a force limiting mechanism may be included in the handle to limit the amount of handle force that is transmitted to the jaws. These force limiting mechanism are complex, however, which leads to increased manufacturing costs. In addition many force limiting mechanisms take up considerable amounts of space in a surgical device. Accordingly, there is a need in the art for a force limiting mechanism that can limit the force a user can apply to the jaws of the surgical instruments that is compact, and simple to manufacture.

BRIEF SUMMARY OF THE INVENTION

The present invention is a force limiting assembly having a reduced number of parts and complexity, thereby reducing assembly time and manufacturing costs. More specifically, a force limiting assembly for a surgical instrument according to the present invention includes a handle and a lever pivotally mounted to the handle at a pivot point. A cantilever spring is positioned in the lever and has a free end spaced apart from the pivot point of the lever. A drive shaft is coupled to the free end of the cantilever spring for axial movement in response to pivoting of the lever about the pivot point that moves the free end of the cantilever spring through a small arc. As the lever is pivoting once the jaws have reached the closed position, force applied to lever causes the cantilever spring to become more fully biased, thereby reducing the amount of force that a user may apply to the drive shaft of the surgical instrument via operation of the lever. The first end of the lever may have two spaced apart arms that extend on opposite sides of the drive shaft. The cantilever spring may have two spaced apart plates that extend on either side of the drive shaft, with each of the two spaced apart plates including a notch formed therein. A pin may extend between the two spaced apart arms of the first end of the lever to engage and hold the cantilever spring in a preload state where the cantilever spring is partially biased. The drive shaft may include a first step fixed thereto and in engagement with the two spaced apart plates of the cantilever spring. The pivoting of the lever about the pivot pin causes the two spaced apart plates of the cantilever spring to push against the first stop so that the drive shaft moves axially. Pivoting of the lever about the pivot pin also causes the cantilever spring to move into a more flexed state where the cantilever spring is more fully biased than the preload state, thereby absorbing some of the force applied by a user to the lever.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
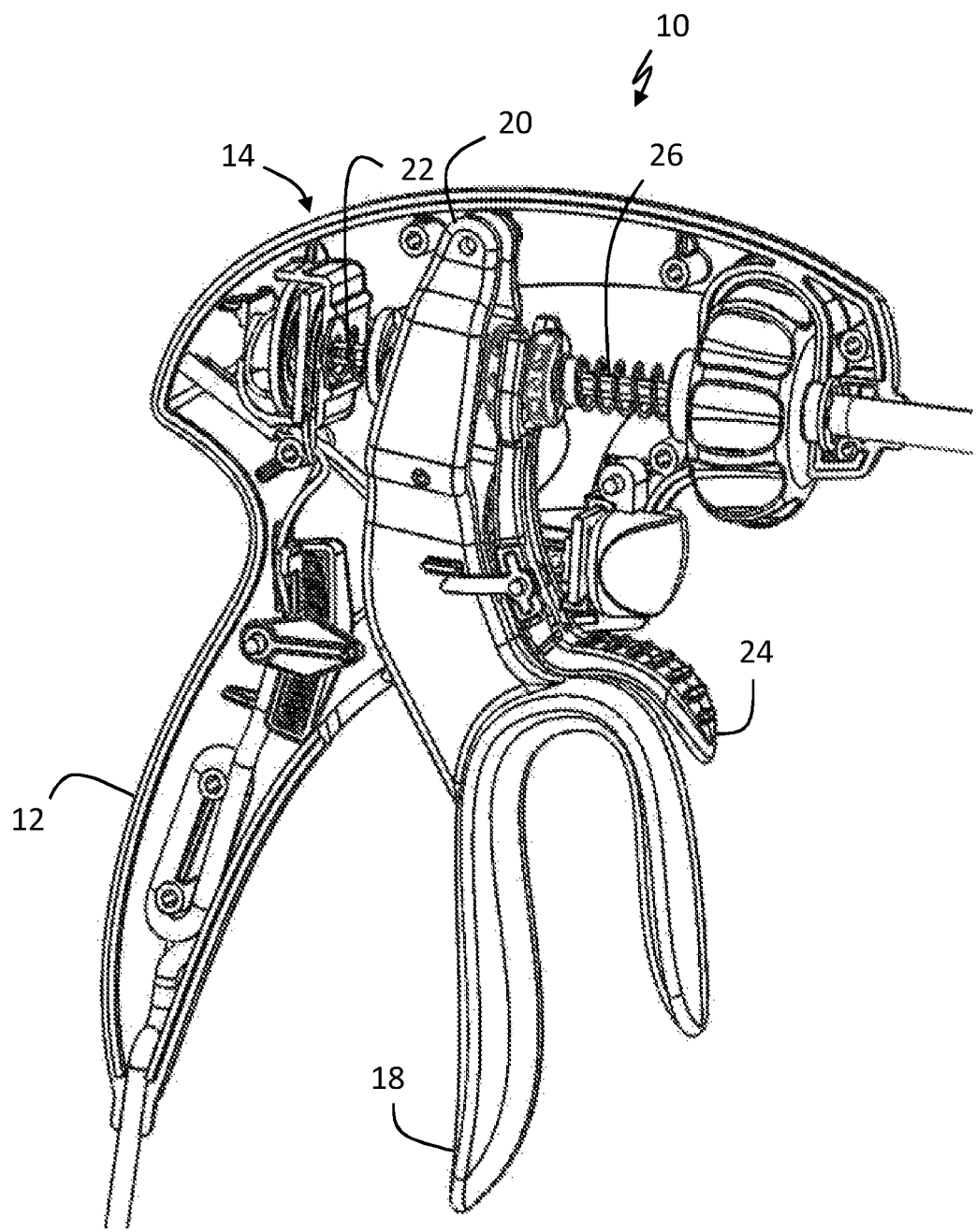
FIG. 1 is an isometric schematic of a handle assembly having a force limiting mechanism according to the present invention.
Figure 2:
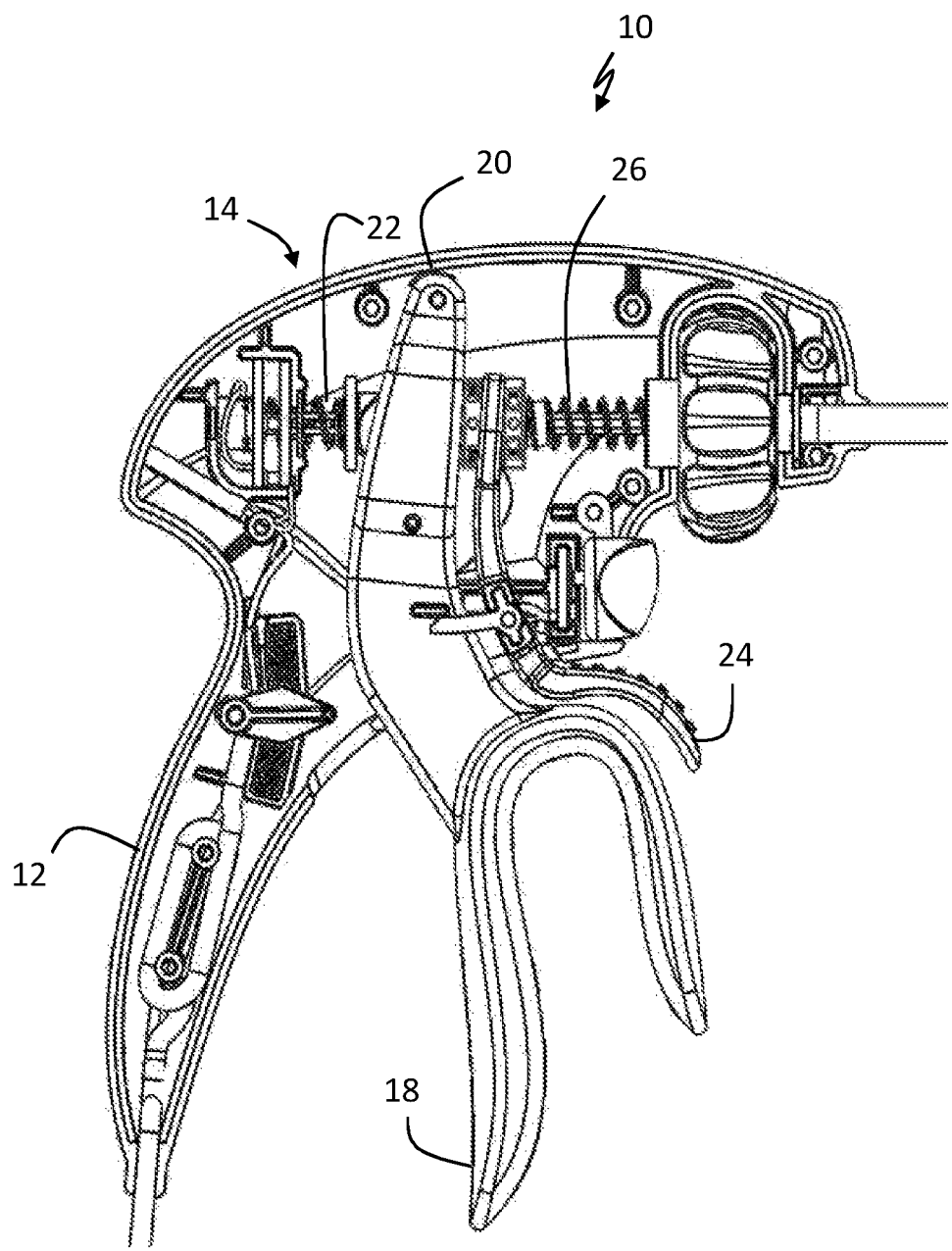
FIG. 2 is a side view of a handle assembly having a force limiting mechanism according to the present invention
Figure 3:
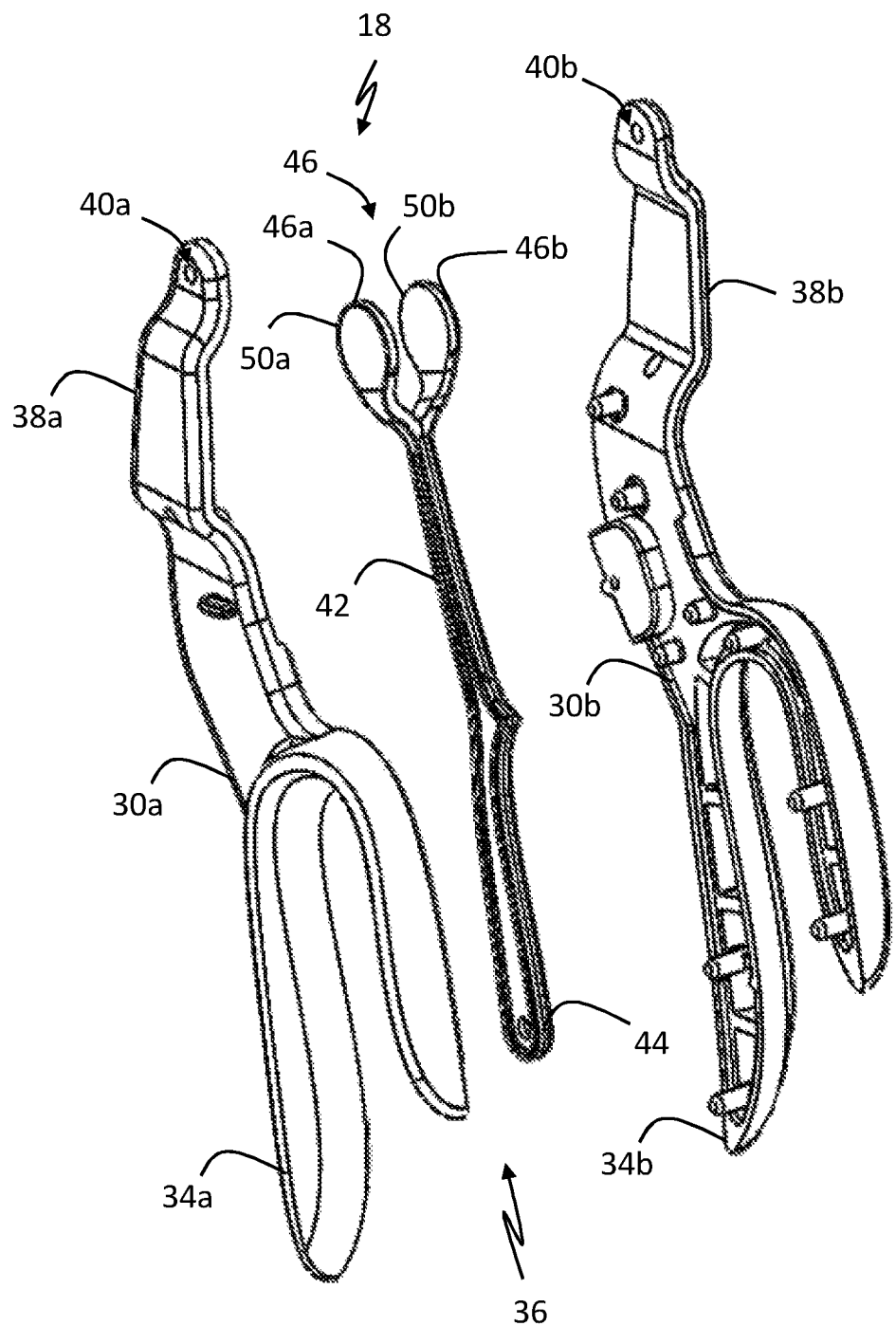
FIG. 3 is an exploded view of a force limiting mechanism according to the present invention.
Figure 4:
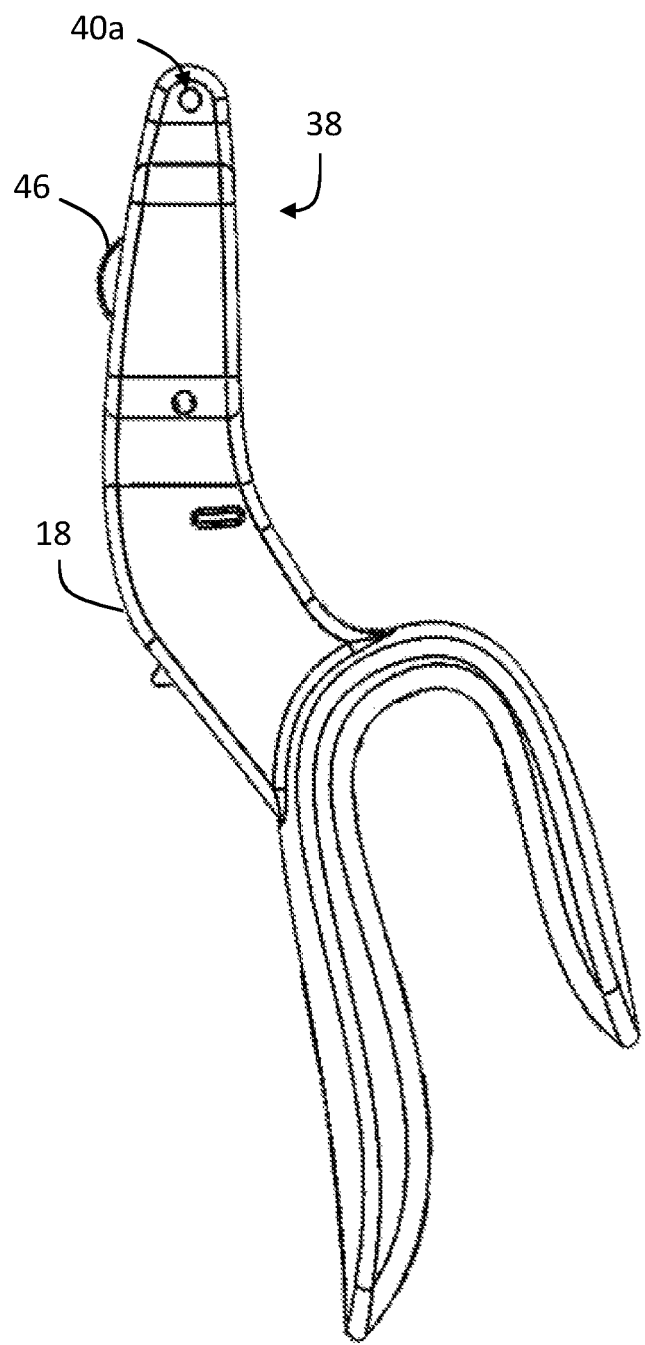
FIG. 4 is a side view of an assembled lever for a force limiting mechanism according to the present invention.

Referring to the figures, wherein like numeral refer to like parts throughout, there is seen in FIGS. 1 and 2, a surgical instrument 10 having a handle 12 with a force limiting mechanism 14 to reduce the amount of force that a user may apply to the jaws 16 of the instrument 10 when operating the lever 18 of handle 12 to close jaws 16. Lever 18 is pivotally mounted at one end 20 within handle 12 and coupled to a drive shaft 22 that is moved longitudinally as lever 18 is pivoted relative to handle 12. Longitudinal movement of drive shaft 22 controls opening and closing of jaws 16 of instrument 10. A second lever 24 may be coupled to the another drive shaft for operating an implement associated with jaws 16, such as a cutting knife that can be extended between jaws 16 to sever any tissue captured therebetween.

Referring to FIGS. 3 through 6, lever 18 comprises two halves 30a and 30b that are coupled together so that the second ends 34a and 34b joint to form a trigger 36 that extends from handle 12 for manual engagement by a user.

Figure 5:
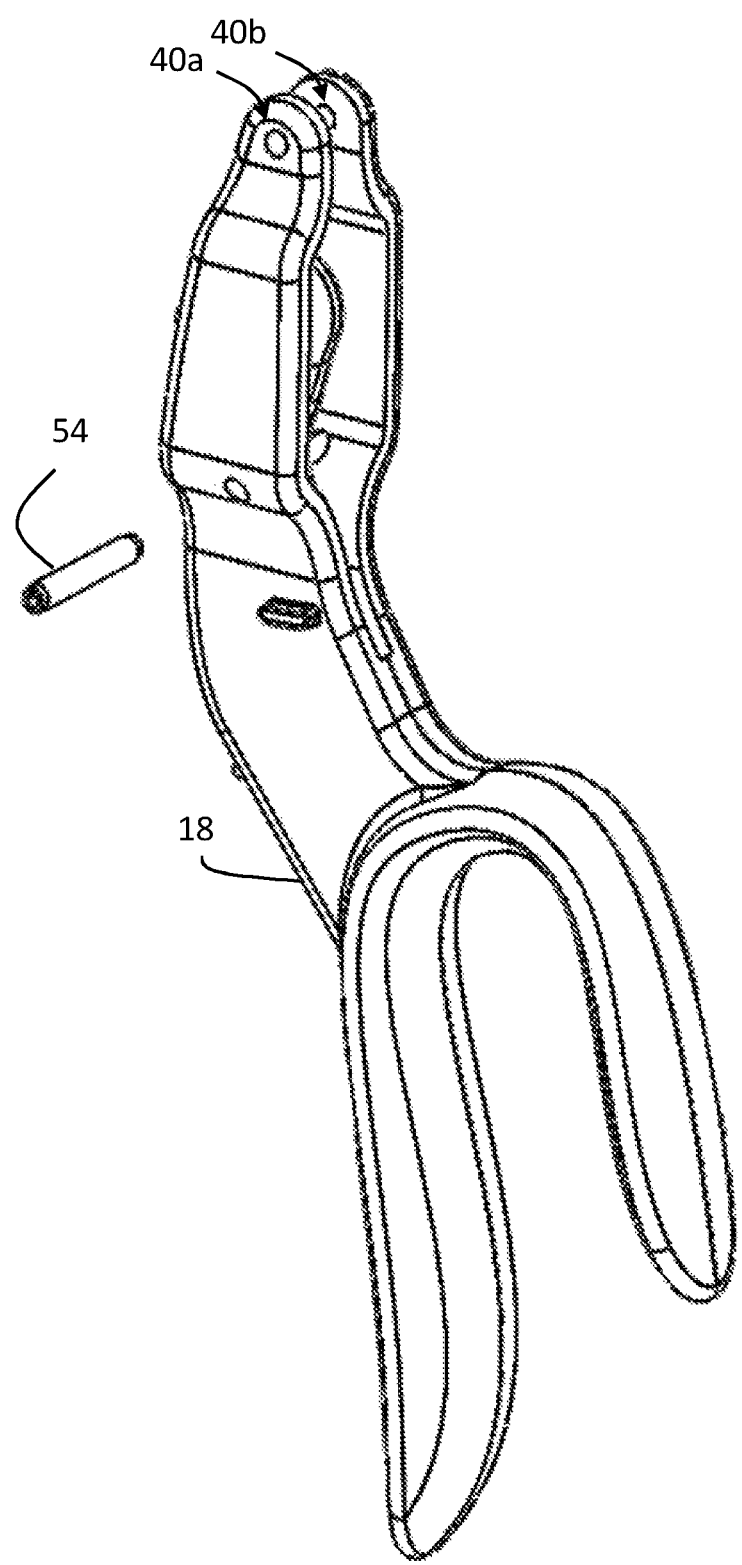
FIG. 5 is a perspective view of a lever assembly and cantilever spring in an unassembled and a preloaded configuration showing the pin insertion according to the present invention.
Figure 6:
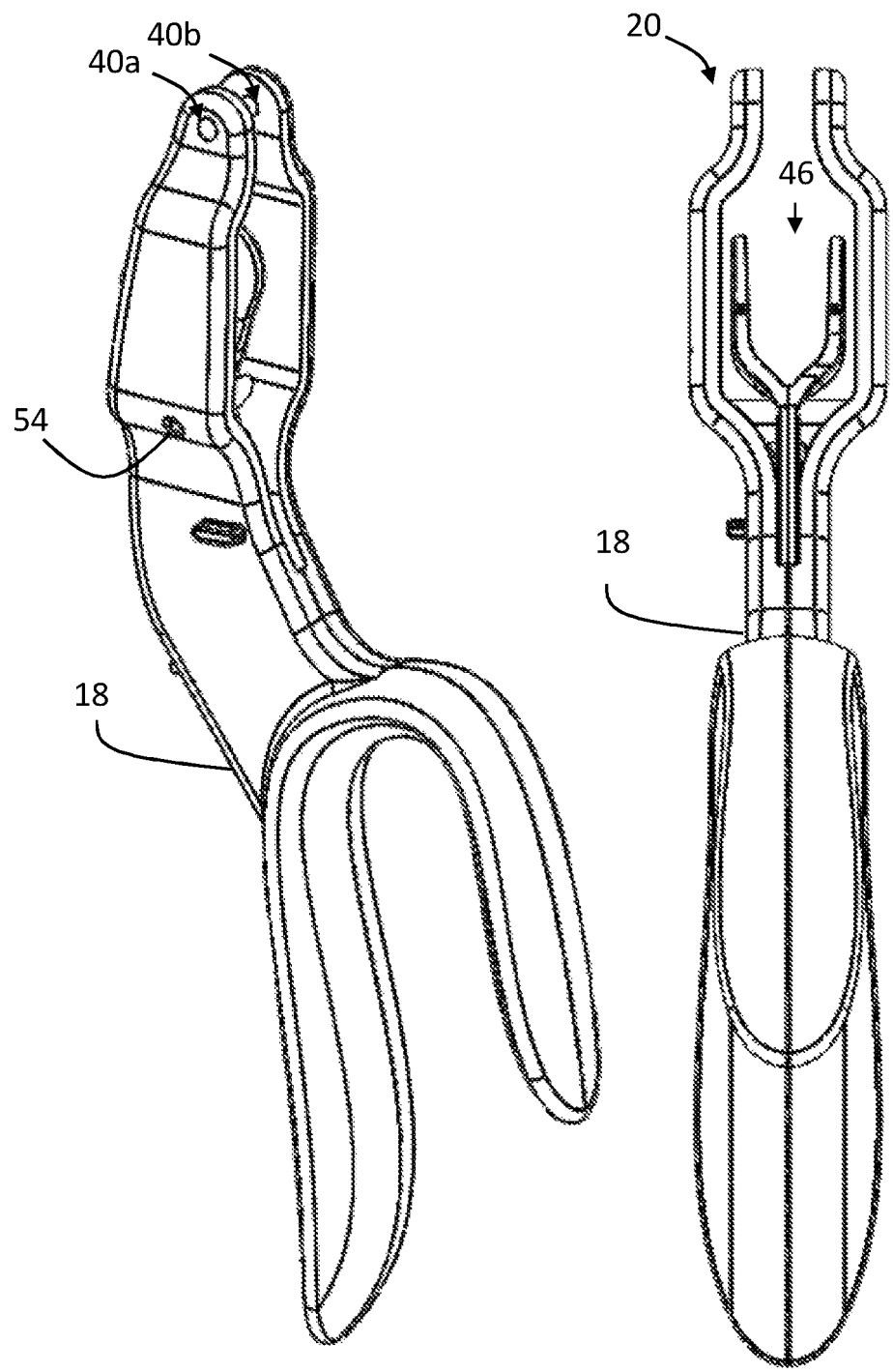
FIG. 6 is a side view of a lever assembly and cantilever spring for a force limiting mechanism in a preloaded configuration according to the present invention.

Two halves 30a and 30b form second end 20 of lever 18 using two spaced apart arms 38a and 38b which together define a fork 38 for pivotal mounting about drive shaft 22 of handle 12. To this end, spaced apart arms 38a and 38b have pivot holes 40a and 40b for pivotal mounting of lever 18 within handle 12. A cantilever spring 42 is positioned between two halves 30a and 30b of lever 18 and coupled therein. Cantilever spring 42 is secured within trigger 36 of lever 18 at one end 44 and extends to define two spaced apart plates 46a and 46b that form a forked free end 46. Forked free end 46 is offset a predetermined distance from fork 38 of lever 18 that is pivotally mounted within handle 12. Plates 46a and 46b of fork 46 have corresponding bearing surfaces 50a and 50b formed therein that face proximally relative to handle 12 when held by a user. Referring to FIG. 5, free end 48 of cantilever spring 42 is held in a partially biased position by a preload pin 54 that extends between two halves 30a and 30b of lever 18 and engages cantilever spring 42 so that cantilever free end 48 of spring 42 is bent distally when positioned between two spaced apart arms 38a and 38b while fixed end 44 of cantilever spring 42 is held within trigger 36 of lever 18.

Figure 7:
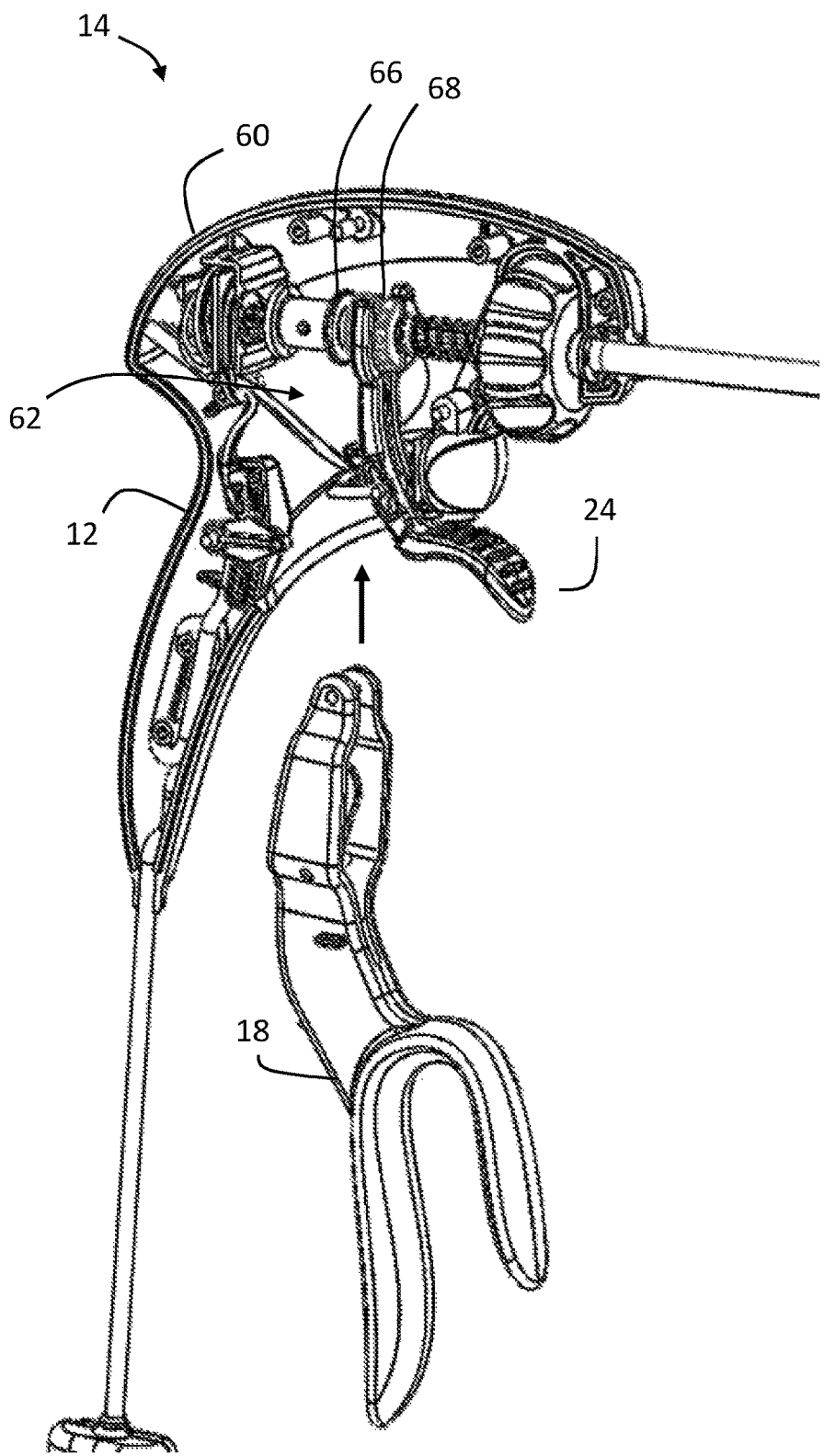
FIG. 7 is an exploded view of a lever assembly incorporated into a handle assembly having a force limiting mechanism according to the present invention.

Referring to FIG. 7, handle 12 comprises a housing 60 that may have two halves coupled together to define a cavity 62 therebetween. Cavity 62 houses drive shaft 22 and force limiting mechanism 14, and is dimensioned to accept lever 18 so that it may be coupled about an intermediate section of drive shaft 22 within handle 12. Lever 18 is pivotally mounted at end 20 within cavity by a pivot pin 64 that extends across cavity 62 through pivot holes 40a and 40b of forked end 40 of lever 18 and fixed to housing 60. Drive shaft 22 extends between forked end 38 of lever and forked end 46 of cantilever spring 42. Drive shaft 22 includes a first stop 66 fixed thereto and positioned proximally to cantilever spring 42 and a second stop 68 fixed thereto and positioned distally of cantilever spring 42 so that cantilever spring 42 is in engagement with both first stop 66 and second stop 68 and bearing surfaces 50a and 50b can move drive shaft 22 axially by pushing against first stop 66.

Figure 8:
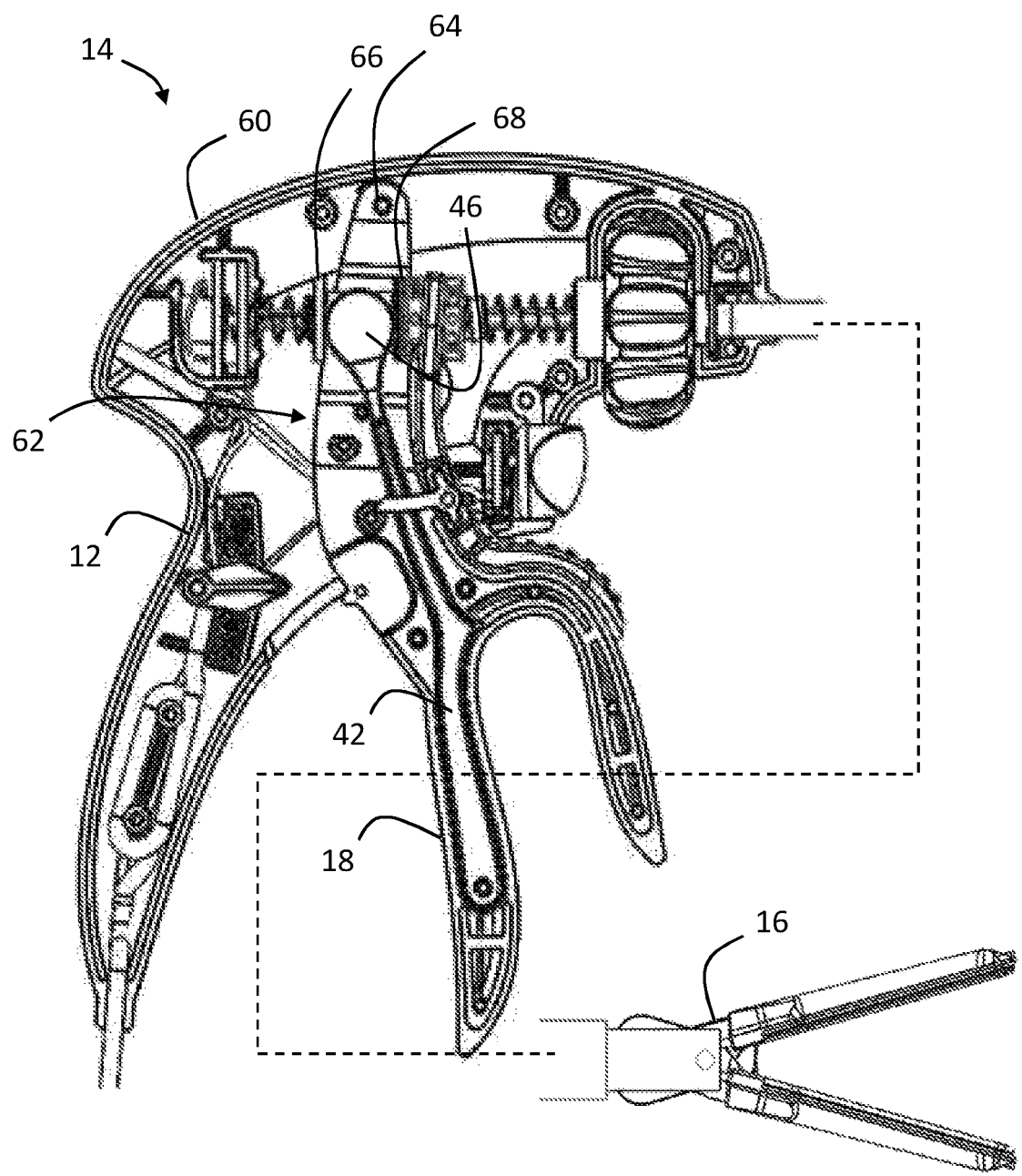
FIG. 8 is a side view of a handle assembly having a force limiting mechanism according to the present invention with the corresponding jaws in the open position.

Referring to FIG. 8, when cantilever spring 42 is in the preload state and lever 18 is in an unactuated position, jaws 16 are in the open position. Lever half 34a is hidden for visibility of the invention. As seen in FIG. 8, lever 18 is in a released position where a user has not applied any force to pivot lever 18 about pivot pin 64. In the released position, cantilever spring 42 is preloaded, but bearing surfaces 50a and 50b of cantilever spring 42 have not applied any force to first stop 66 and thus drive shaft 22 has not moved axially in a manner that would cause jaws 16 to close.

Figure 9:
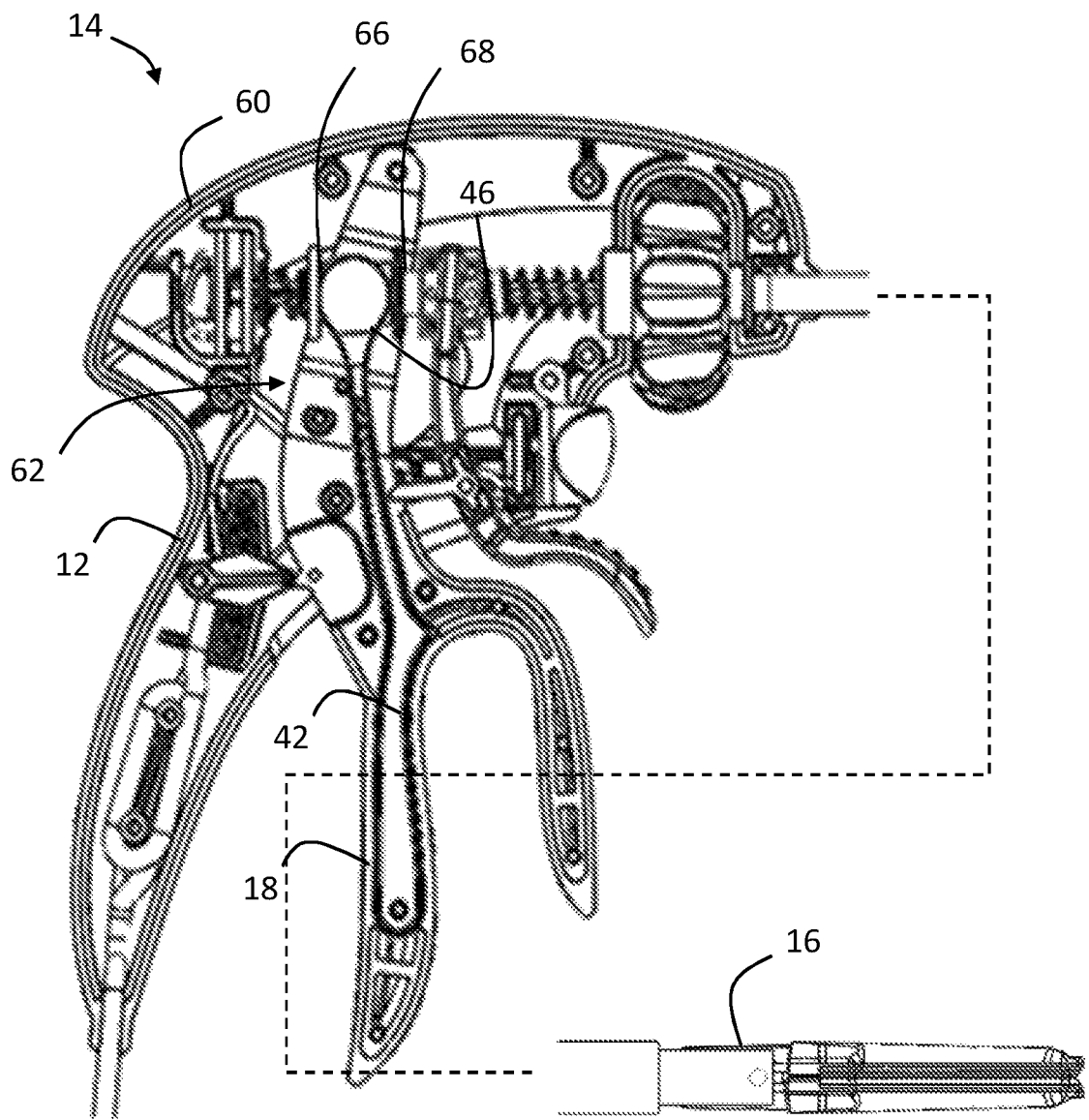
FIG. 9 is a side view of a handle assembly having a force limiting mechanism according to the present invention with the corresponding jaws in the closed position.

Referring to FIG. 9, a user has manually applied a force to lever 18 so that lever 18 partially pivots about pivot pin 64 and drives drive shaft 22 to close jaws 16. As lever 18 is pivoted, free end 46 of cantilever spring 42 will engage and push against first stop 66 to move drive shaft 22 proximally so that jaws 16 are driven by drive shaft 22 into the closed position. As explained above, forked free end 46 is offset a predetermined distance from the pivot point of fork 38 of lever 18 within handle 12. As a result, pivoting of lever 18 about pivot pin 64 will move forked free end 46 of cantilever spring 42 through a small arc within handle 12. Pivoting of lever 18 thus causes free end 46 of cantilever spring 42 to bias first stop 66 of drive shaft 22 proximally so that drive shaft 22 translates distally along its longitudinal axis. This proximal movement of drive shaft 22 translates into a closing of jaws 16 as the opposing end of drive shaft 22 is interconnected to jaws 16 such that proximal movement of drive shaft 22 forces each jaw member of jaws 16 to pivot into the closed position. For example, drive shaft 22 may be coupled to each jaws 16 via a pin extending through slots positioned proximally of the pivot point of jaws 16 so that axial movement of pin causes jaws 16 to close. It should be recognized that other mechanical approaches may be used to translate the axial movement of drive shaft 22 into closing of jaws 16 without impacting the design of force limiting mechanism 14.

Figure 10:
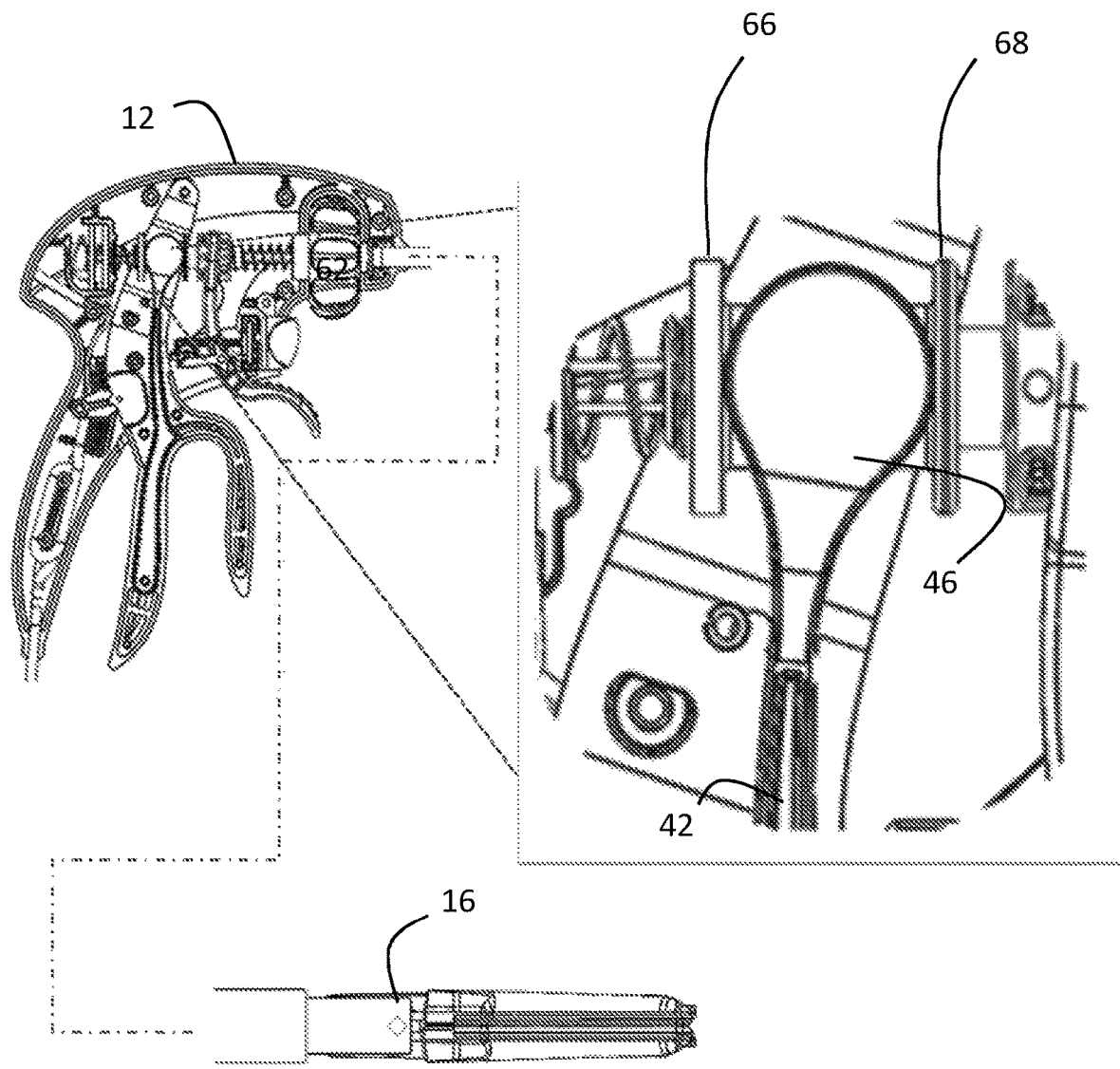
FIG. 10 is a side view of a handle assembly having a force limiting mechanism according to the present invention with the corresponding jaws in the closed position and with additional force applied to the lever beyond what is needed to move the jaws in the closed position.

Referring to FIG. 10, pivoting of lever 18 beyond the point where jaws 16 are fully closed will cause the additional manual force to be translated into additional flexing of cantilever spring 42 so that cantilever spring 42 becomes flexed beyond the initial preload of FIG. 8. The additional flexing of cantilever spring 42 provides user feedback as to the force being applying to jaws 16 and, more importantly, limits the amount of force applied to lever 18 that is translated into movement of drive shaft 22 as the force is translated into flexing of cantilever spring 42 rather than additional movement of drive shaft 22. Thus, any force applied to lever 18 that extends beyond what is necessary to close jaws 16 can be absorbed into additional flexing of cantilever spring 42, thereby limiting that amount of force applied to jaws 16 and preventing an over-application of manual force that could damage instrument 10.

It should be recognized that amount of force needed for closure of jaws 16, i.e., the amount of force to be limited, as well as the distance of motion of drive shaft 22, and the amount of force over the limit amount that can be absorbed may be adjusted by varying the offset of cantilever spring 42 from pivot pin 64, the design and material used for cantilever spring 42, etc. Thus, force limiting mechanism 14 may be adjusted to adapt to whatever conditions are desired for surgical instrument 10. Moreover, while the present invention has been illustrated in combination with an electrosurgical vessel sealer, the force limiting assembly would also be useful in combination with any other surgical instrument having a user handle and lever that is used to provide a force. For example, clip appliers, graspers, dissectors, and other handle and lever operated instruments could also benefit from a force limiting assembly according to the present invention.

What is claimed is:

1. A force limiting assembly for a surgical instrument, comprising:
    a handle;
    a lever pivotally mounted to the handle at a pivot point at a first end and extending out of the handle to define a trigger at an opposing end;
    a cantilever spring positioned in the lever and having a free end spaced apart from the pivot point; and
    a drive shaft coupled to the free end of the cantilever spring for axial movement in response to pivoting of the lever about the pivot point.

2. The force limiting assembly of claim 1, wherein the first end of the lever has two spaced apart arms.

3. The force limiting assembly of claim 2, wherein two spaced apart arms of the first end of the lever extend on opposite sides of the drive shaft.

4. The force limiting assembly of claim 3, wherein the cantilever spring has two spaced apart plates.

5. The force limiting assembly of claim 4, wherein the two spaced apart plates extend on either side of the drive shaft.

6. The force limiting assembly of claim 5, wherein a pivot pin extends between the two spaced apart arms of the first end of the lever and the cantilever spring to hold the cantilever spring in a preload state where the cantilever spring is partially biased position.

7. The force limiting assembly of claim 6, wherein the drive shaft includes a first stop fixed thereto and in engagement with the two spaced apart plates of the cantilever spring.

8. The force limiting assembly of claim 7, wherein pivoting of the lever about the pivot pin causes the two spaced apart plates of the cantilever spring to push against the first stop so that the drive shaft moves axially.

9. The force limiting assembly of claim 8, wherein pivoting of the lever about the pivot pin causes the cantilever spring to move into a flexed state where the cantilever spring is further biased than in the preload state.

10. A method of limiting an amount of force applied to a surgical instrument having a handle and a lever pivotally mounted to the handle, comprising the steps of:
   positioning a cantilever spring within the lever so that the cantilever spring has a free end spaced apart from a pivot point of the lever relative to the handle; and
   coupling the cantilever spring with a drive shaft of the surgical instrument so pivoting of the lever about the pivot point causes the cantilever spring to impart a force to the drive shaft to move the drive shaft axially.

11. The method of claim 10, wherein the cantilever spring is partially biased prior to movement of the lever relative to the handle.

12. The method of claim 11, wherein the cantilever spring is further biased when movement of the lever exceeds a predetermined amount of desired movement of the drive shaft.

13. The method of claim 12, wherein the cantilever spring is positioned between two stops fixed to the drive shaft.

* * * * *